United States Patent [19]
Goebel

[11] Patent Number: 6,143,551
[45] Date of Patent: Nov. 7, 2000

[54] DELIVERY OF POLYPEPTIDE-ENCODING PLASMID DNA INTO THE CYTOSOL OF MACROPHAGES BY ATTENUATED LISTERIA SUICIDE BACTERIA

[75] Inventor: Werner Goebel, Gerbrunn, Germany

[73] Assignee: Schering Aktiengesellschaft, Berlin, Germany

[21] Appl. No.: 08/999,391

[22] Filed: Dec. 29, 1997

[51] Int. Cl.⁷ .............................. C12N 1/21; C12N 15/63; A61K 35/00
[52] U.S. Cl. .................... 435/252.3; 435/320.1; 424/200.1; 424/93.2; 424/93.4
[58] Field of Search .............. 435/320.1, 252.3; 424/200.1, 93.2, 93.4

[56] References Cited

U.S. PATENT DOCUMENTS 5,763,251  6/1998  Gasson ..................................... 435/115

OTHER PUBLICATIONS

Verma et al. (Sep. 1997) Nature, vol. 389, 239–242.

Bachmann et al. (1994) Current Opinion in Immunology, vol. 6, 320–326.

*Primary Examiner*—Deborah Crouch
*Assistant Examiner*—Anne Marie S. Beckerleg
*Attorney, Agent, or Firm*—Millen, White, Zelano, & Branigan, P.C.

[57] ABSTRACT

The invention relates to the introduction of DNA or RNA sequences into a mammalian cell to achieve controlled expression of a polypeptide. It is therefore useful in gene therapy, vaccination, and any therapeutic situation in which a polypeptide should be administered to a host or cells of said host, as well as for the production of polypeptides by mammalian cells, e.g., in culture or in transgenic animals.

14 Claims, 2 Drawing Sheets

DELIVERY OF POLYPEPTIDE-ENCODING PLASMID DNA INTO THE CYTOSOL OF MACROPHAGES BY ATTENUATED LISTERIA SUICIDE BACTERIA

BACKGROUND OF THE INVENTION

The present invention relates to the introduction of DNA and RNA sequences into a mammalian cell to achieve controlled expression of a polypeptide. It is therefore useful in gene therapy, vaccination, and any therapeutic situation in which a polypeptide should be administered to a host or cells of said host, as well as for the production of polypeptides by mammalian cells, e.g., in culture or in transgenic animals.

Gene therapy is a set of approaches for the treatment of human disease based on the transfer of genetic material (DNA/RNA) into an individual. Gene delivery can be achieved either by direct administration of gene-containing viruses or DNA to blood or tissues, or indirectly through the introduction of cells manipulated in the laboratory to harbor foreign DNA (see, e.g. U.S. Pat. No. 5,399,346). The tremendous promise of gene therapy is stymied by inefficient gene transfer. G. Parmiani, F. Arienti, J. Sule-Suso, C. Melani, M. P. Colombo, V. Ramakrishna, F. Belli, L. Mascheroni, L. Rivoltini and N. Cascinelli, Cytokine-based gene therapy of human tumors, An Overview, Division of Experimental Oncology D, Instituto Nazionale Tumori, Milan, Italy, *Folia Biol (Phraha)* 42: 305–9 (1996); P. Hess, Gene therapy: a review, American Association of Clinical Chemistry, Laboratory Corporation of America, Louisville, Ky., 40213, USA, *Clin Lab Med* 16: 197–211 (1996); and N. Miller and R. Vile, Targeted vectors for gene therapy, Laboratory of Cancer Gene Therapy, Rayne Institute, St. Thomas' Hospital, London, United Kingdom, *FASEB J* 9: 190–9 (1995).

The clinical application of gene therapy, as well as the utilization of recombinant retrovirus vectors, has been delayed because of safety considerations. Integration of exogenous DNA into the genome of a cell can cause DNA damage and possible genetic changes in the recipient cell that could predispose to malignancy. A method which avoids these potential problems would be of significant benefit in making gene therapy safe and effective.

Vaccination with immunogenic proteins has eliminated or reduced the incidence of many diseases; however there are major difficulties in using proteins associated with other pathogens and disease states as the immunogen. Many protein antigens are not intrinsically immunogenic. More often, they are not effective as vaccines because of the manner in which the immune system operates.

The immune system of mammalians consists of several interacting components. The best characterized and most important parts are the humoral and cellular branches. Humoral immunity involves antibodies, proteins which are secreted into the body and which directly recognize an antigen. The cellular system, in contrast, relies on special cells which recognize and kill other cells which are producing foreign antigens. This basic functional division reflects two different strategies of immune defense. Humoral immunity is mainly directed at antigens which are exogenous to the animal whereas the cellular system responds mainly to antigens which are actively synthesized within the cells of the animal.

Antibody molecules, the effectors of humoral immunity, are secreted by special cells, B cells, in response to antigen. Antibodies can bind to and inactivate antigen directly (neutralizing antibodies) or activate other cells of the immune system to destroy the antigen.

Cellular immune recognition is mediated by a special class of lymphoid cells, the cytotoxic T cells. These cells do not recognize whole antigens but instead they respond to degraded peptide fragments thereof which appear on the surface of the target cell bound to proteins called class I major histocompatibility complex (MHC) molecules. Essentially all nucleated cells have class I molecules. It is believed that proteins produced within the cell are continually degraded to peptides as part of normal cellular metabolism. These fragments are bound to the MHC molecules and are transported to the cell surface. Thus the cellular immune system is constantly monitoring the spectra of proteins produced in all cells in the body and is poised to eliminate any cells producing foreign antigens.

A large number of disease states can benefit from the administration of therapeutic and/or prophylactic polypeptides. Such polypeptides include e.g. lymphokines, such as interleukins, tumor necrosis factor, the interferons; growth factors, such as nerve growth factor, and human growth hormone; tissue plasminogen activator; factor VIII:C; granulocyte-macrophage colony-stimulating factor; erythropoietin; insulin; calcitonin; thymidine kinase; and the like. Moreover selective delivery of toxic peptides (such as ricin, diphtheria toxin, or cobra venom factor) to diseased or neoplastic cells can have major therapeutic benefits.

Vaccination by intramuscular injection of antigen-encoding DNA is a promising approach (J. J. Donnelly, J. B. Ulmer, M. A. Liu, *J. Immunol. Methods* 176, 145 (1994); R. M. Conry et al., *Cancer Res.* 54, 1164 (1994); C. H. Hsu et al., *Nature Med.* 2, 540 (1996); R. E. Tascon et al., *Nature Med.* 2, 888 (1996)), but how an immune response is accomplished is not fully understood, although bone marrow-derived antigen presenting cells (APC), rather than myocytes, seem to induce the immune responses after migration to the spleen (M. Corr et al., *J. Exp. Med.* 184, 1555 (1996)). Intramuscular injection of pure plasmid DNA into the host still poses several problems: (i) The efficiency of the DNA-uptake seems to be quite low and dose-dependent, which means that a large amount of plasmid DNA has to be injected to elicit a protective immune response (R. R. Deck et al., *Vaccine*, 15, 71 (1997)). This in turn might lead to adverse effects through immune stimulation by bacterial DNA-sequences (D. S. Pisetsky, *J. Immunol.* 156, 421 (1996)). (ii) Intramuscular DNA injection does not seem to induce immune responses at distant mucosal surfaces (R. R. Deck et al., *Vaccine*, 15, 71 (1997)). (iii) There are only low numbers of antigen-presenting cells (APC) in the muscle tissue and thus protection against infectious agents after intramuscular injection of plasmid DNA may only be possible with immunologically very potent antigens. This makes it desirable to deliver the antigen-encoding DNA directly to splenic APC.

Recently, attenuated *Shigella flexneri* (D. R. Sizemore, A. A. Branstrom, J. C. Sadoff, *Science* 270, 299 (1995)) and invasive *Escherichia coli* (P. Courvalin, S. Goussard, C. Grillot-Courvalin, *Life Sciences* 318, 1207 (1995)) were used for plasmid delivery in cultured mammalian cells, in guinea pigs and in mice. *Shigella flexneri* and *E. coli* are Gram-negativ bacteria, though, which contain Lipopolysaccharide (LPS), exhibiting strong endotoxic effects in mammals. Furthermore, these bacteria are only suiteable for the introduction of therapeutic molecules into certain cell types, e.g., enterocytes (P. J. Sansonetti. Pathogenesis of shigellosis. *Curr. Top. Microbiol. Immunol.*, 180:1–143(1992).

Thus, new techniques were needed to solve the above-described problems associated with immunization, gene therapy, and delivery of therapeutic polypeptides to cells, both ex vivo and in vivo.

BRIEF DESCRIPTION OF THE FIGURES

Various other features and attendant advantages of the present invention will be more fully appreciated as the same becomes better understood when considered in conjunction with the accompanying figures, wherein:

FIG. 1(A+B) shows expression of the cDNA for gfp and the ply118-gene under the control of the actA-promoter of *L. monocytogenes* in bacteria during culture in BHI or infection of macrophages.

(A) Emission spectra and fluorescence intensities of extracellularly grown *L. monocytogenes* EGD wild-type (c), EGD(pERL3501) carrying multiple copies of prfA (a), mutants Δ2 (b) and ΔprfA (d), all carrying the gfp gene under the control of $P_{actA}$. $2 \times 10^6$ bacteria grown logarithmically in BHI medium were washed in phosphate buffered saline (PBS) and resuspended in 2 ml PBS. The emission spectra were recorded from 500 to 550 nm with a fixed excitation wavelength of 481 nm in a SPEX FluoroMax fluorimeter. *L. monocytogenes* EGD without the gfp plasmid was used as a blank. Photons measured at the expected peak of 507 nm are given in arbitrary units (AU).

(B) Intracellular expression of the ply118 gene in *L. monocytogenes* mutant Δ2 under control of $P_{actA}$ in infected macrophage cell lines J774A.1 and P388D$_1$ leads to partial inactivation of *L monocytogenes* in the cytosol of infected cells. Infection of macrophages with Δ2(p3L118) and Δ2(pcDNA3L) was done in complete medium (12) containing 10 μg/ml tetracycline (Sigma) at a MOI of 1:1 (~$2.5 \times 10^4$ macrophages per well). Macrophage cells were incubated for 60 min, washed three times with PBS and cultured in complete medium supplemented with 10 μg/ml gentamicin (Boehringer) and 10 μg/ml tetracycline. Macrophages were lysed as indicated and viable bacterial counts determined by plating serial dilutions on BHI-agar. Combined data from three independent experiments are shown.

FIG. 2(A–C) shows expression of heterologous genes in macrophages using *L monocytogenes* mediated plasmid DNA delivery.

(A) Expression of GFP in P388D$_1$ cells infected with *L. monocytogenes* mutant Δ2 carrying plasmids p3LGFP118, p3LGFP [in the presence or absence of penicillin (100 IU/ml) and streptomycin (100 μg/ml) (P/S, Gibco) from 2 h p.i. onwards to lyse intracellular bacteria] and the control plasmid pcDNA3L. $10^6$ macrophages per flask were infected with bacteria at a MOI of 50:1. Medium was changed every 24 h. Cells expression GFP were determined by fluorescence microscopy of at least $5 \times 10^4$ cells per flask at each time point. Combined data of two replicate experiments are shown.

(B) CAT-expression in P388D$_1$ cells infected with *L. monocytogenes* strain Δ2 harboring plasmids p3LCAT118, p3LCAT (with and without addition of penicillin and streptomycin) and control plasmid pcDNA3L. Cells were harvested and CAT-activities of cell lysates containing 100 μg of total protein [Bradford assay (Bio-Rad)] were determined in accordance with the manufacturer's instruction (Invitrogen) with purchased CAT-enzyme (Boehringer) as standard. Combined data of two replicate experiments are shown.

(C) Presentation of the OVA-epitope (257–264) after delivery by Δ2(p3LOVA118). Bacteria were added to adherent C57BL/6-derived bone marrow macrophages (BMM) ($10^5$ per well) which were previously cultured in Dulbecco's modified Eagle's medium (DMEM including 10% FCS, 2 mM L-glutamine, 1 mM sodium pyruvate) containing 500 U/ml IFN-g and 10 μg/ml tetracycline for 24 h. After phagocytosis for 1 h, 50 μg/ml gentamicin was added and the infected macrophages were incubated at 37° C. in the presence of 10% $CO_2$ for 24 h. The cells were washed three times and fixed in 1% paraformaldehyde in PBS. RF33.70 T-T hybridoma cells specific for OVA (257–264)-K$^b$ ($10^5$ per well) were then added in RPMI 1640 supplemented with 10% FCS, 2 mμ L-glutamine and 50 μg/ml gentamicin for 24 h. The amount of secreted interleukin-2 (IL-2) after 48 h was quantified by $^3$H-thymidine incorporation of IL-2 dependent CTLL cells as previously described (20). The results are representative for three individual experiments.

SUMMARY OF THE INVENTION

The invention relates to an attenuated invasive intracellular bacterium capable of infecting a mammalian host or cell thereof, but having a decreased ability in intra- and intercellular movement in sad host as compared to a wild type bacterium, transformed with (a) a promoter activated when said bacterium is present in the cytosol of a host cell, operably linked to a structural gene or fragment thereof, encoding a polypeptide which is lethal to the bacterium, (b) a host cell-compatible promoter, operably linked to a structural gene or fragment thereof, encoding a polypeptide which has therapeutic and/or prophylactic properties, e.g., as an antigen, wherein (a) and (b) can be on the same plasmid or different plasmids or (a) can be integrated into the bacterial chromosome.

The invasive bacterium can be utilized in various ways, including as a vaccine, and, in in vivo and ex vivo gene therapy.

By attenuated invasive bacteria, it is meant, e.g., a bacterium which can still invade a host, or cells thereof, but which is not pathogenic. Attenuation can be achieved routinely, e.g., by mutation. See, e.g., (T. Maniatis, et al. Molecular Cloning: A Laboratory Manual, Second Edition, Cold Spring Harbor, N.Y. (1989)). For instance, attenuation can be caused by mutating the bacterial genes which encode for pathogenic and/or toxic polypeptides. Such a mutation can be achieved randomly, e.g., by chemical modification and selected later, e.g., for loss of function, or it can be site directed, e.g., by deletion, insertion or point mutations, to eliminate the function of certain genes that encode polypeptides which lead to pathogenesis. For example, by deleting an entire operon by chromosomal deletion, e.g., the attenuated *Listeria monocytogenes* mutant strain Δ2 is a derivative of the fully virulent wild-type strain EGD and lacks the entire lecithinase operon consisting of the genes mpl, actA and plcB due to a chromosomal deletion. Due to the deletion of this operon the inflammatory response caused by *Listeria monocytogenes* during infection of a mammalian host is significantly reduced.

The attenuated bacteria according to this invention are intracellular bacteria, such as Salmonella, Yersinia, Renibacterium and Listeria capable of intracellular growth (C. Coynault, V. Robbe-Saule, and F. Norel, Virulence and vaccine potential of *Salmonella typhimurium* mutants deficient in the expression of the RpoS (sigma S) regulon, *Molecular Microbiology* 22, 149–160 (1996); E. L. Hohmann, C. A. Oletta and S. I. Miller, Evaluation of a phoP/phoQ-deleted, aroA-deleted live oral *Salmonella typhi* vaccine strain in human volunteers, *Vaccine* 14, 19-14 (1996); K. L. Karem. S. Chatfield, N. Kuklin and B. T. Rouse, Differential induction of carrier antigen-specific immunity by *Salmonella typhimurium* live-vaccine strains after single mucosal or intravenous immunization of BALB/c mice. *Infection and Immuity* 63, 4557–4563 (1995); D. O'Callaghan, D. Maskell, F. Y. Liew, C. S. F. Easmon and G. Dougan, Characterization of aromatic- and purine- defendant *Salmonella typhimurium*: attenuation, persistence and ability to induce protective immunity in BALB/c mince, *Infection and Immunity* 56, 419–423 (1988); D. F. Sigwart, B. A. Stocker and J. D. Clements, Effect of a purA mutation on efficacy of Salmonella live-vaccine vectors, *Infection and Immunity* 57, 1858–61 (1989); and K. Sinha, P. Mastroeni, J. Harris, R. D. de Hormaeche and C. E. Hormaeche, *Salmonella typhimurim* aroA, htrA, and aroD htrA mutants cause progression infections in athymic (nu/nu) BALB/c mice, *Infection and Immunity* 65, 1566–1569 (1997)).

In a preferred embodiment of the present invention, the attenuated bacterium is a mutant of wild-type Listeria which invades host cells and is released into the cytosol of the infected cells with similar efficiencies as the wild-type strain, but is impaired in intra- and intercellular movement, i.e., the mutant *Listeria monocytogenes* strain Δ2 is unable to polymerise host cell actin in the cytosol which *Listeria monocytogenes* wild type strain uses for its movement inside the host cell. Furthermore, due to the deletion of plcB, the bacteria is unable to lyse the host cell membranes which the wild type strain lyses upon entering neighbouring cells. Mutant bacteria are therefore unable to move from one infected cell into a neighboring cell (cell-to-cell spread). This illustrates a decreased ability (e.g., as compared to wild type strains) in intra- and inter-cellular movement.

In a more preferred embodiment of the invention, the attenuated bacterium can cause less inflammatory reaction than the wild-type strain, e.g., at least 50%, preferable 70%, more preferably 90% less inflammation as measured in an infected mouse.

In a preferred embodiment, the attenuated bacterium is a mutant of *L. monocytogenes* which invades the host and is released into the cytosol of the infected cells with similar efficiencies as the wild-type strain, but it is not pathogenic, i.e., it doesn't cause a disease. In a more preferred embodiment, the mutant bacterium is *L. monocytogenes* and lacks the entire lecithinase operon containing the genes mpl, actA and plcB.

*L. monocytogenes* is able to invade a large variety of cell types, especially when cultured in vitro (M. Kuhn and W. Goebel, *Genetic Engineering*, Vol. 17. Edited by J. K. Setlow Plenum Press, New York (1995)). A mammalian host could be, i.e., human, dog, cat, cows, sheep or pigs, and the like.

In the present invention, a structural gene or fragment thereof encoding a polypeptide which is lethal to the bacterium is any polypeptide which when expressed in the bacterium will result in the release of plasmid DNA and death of said bacterium, e.g., by lysis of the bacterium. Such a polypeptide can, e.g., cause autolysis of the bacterium in the cytosol of the host cell. The polypeptide can be a bacteriophage lysin, preferable the gene product of ply 118 or other Listeria-phage-encoded lysins, e.g., the mureinhydrolase encoded by the iap gene of *L. monocytogenes* or other iap-related genes especially iap of *L. grayi*. The lysis protein PLY 118 is a late gene product of the Listeria bacteriophage A118 necessary for the release of progeny phages. PLY 118 is a highly active, cell wall-hydrolyzing enzyme specific for Listeria (M. J. Loessner, G. Wendlinger, S. Scherer, *Mol. Microbiol.* 16, 1231 (1995)).

By a promoter activated when it is present in an invasive bacterium which is in the cytosol of a host cell, it is meant any promoter which, when the bacteria is inside the infected cell, is (under the control of a transcription activator which is) preferentially turned on, driving its transcription. For example, the *L. monocytogenes* promoter $P_{actA}$ can be used. The $P_{actA}$ promoter is controlled by the transcription activator PrfA which regulates most of the known virulence genes of *L. monocytogenes* and is specifically activated in the cytosol of the infected host cells to interact with the actA promoter. Other promoters which can be used according to the present invention are, e.g., other promoters of *L. monocytogenes*, such as those controlling the expression of inlC and other genes for small internalins (F. Engelbrecht, S.-K Chun, C. Ochs, J. Hess, F. Lottspeich, W. Goebel, and Z. Sokolovic, Mol. Microbiol. 21:823–837(1996); F. Engelbrecht, C. Dickneite, R. Lampidis, M. Goetz, U. DasGupta, and W. Goebel, "Sequence comparison of the chromosomal regions carrying the internalin C gene (inlC) of *Listeria monocytogenes* and *Listeria ivanovii*" in press (1998).

In a further preferred embodiment the attenuated invasion bacterium is *L monocytogenes* and the promoter activated, when it is present in an invasive bacterium which is in the cytosol of a host cell, is $P_{actA}$, operably linked to the gene ply 118, which encodes the lysis protein PLY 118.

The present invention also relates to a method of vaccination and/or gene therapy, wherein the gene encoding a desired polypeptide, e.g., an antigen, is operably linked to a promoter which is host cell-compatible and present in the bacterium. According to the invention, both expressible DNA and mRNA, as well as non-expressible DNA and RNA, e.g., antisense oligodeoxynucleotides (ODNs) (R. W. Wagner, *Nature* 372, 333 (1994); A. Craig, D. Vanstone and S. Agrawal, *Exp. Opin. Ther. Patents* 7, 1175 (1997) or ribozymes can be used.

A host cell-compatible promoter according to the present invention is e.g., any promoter or promoter/enhancer that is able to initiate sufficient transcription of the homologous or heterologous gene or fragment thereof, which is operably linked to it, in said host cell. Any promoter or promoter/enhancer can be used which results in expression of an amount of a polypeptide useful for its intended purpose, e.g., to achieve a prophylactic and/or therapeutic result and/or to provoke an immune response. Some examples of mammalian cells that can be used according to this invention are, e.g., epithelial cells, fibroblasts, dendritic cells, and macrophages with such promototers as, e.g., promoter/enhancer from the cytomegalovirus (CMV) immediate early gene 1 or the rous sarcoma virus long terminal repeat or the simian virus 40 promoter or the adenovirus 2 major late promoter or the mouse mammary tumor virus promoter (MMTV). Viral gene promoters are usually stronger than cellular housekeeping gene promoters and have been shown to give higher levels of reporter gene expression in vivo after injection into mouse muscle (Manthrope, M., Cornefert-Jensen, F., Hartikka, J., Felgner, J., Rundell, A., Margalith, M., and Dwarrki, V., Gene therapy by intramuscular injection of plasmid DNA; studies on firefly luciferase gene expression in mice. *Hum. Gen. Ther.* 4:419–431 (1993))
Nonviral promoters can also be used, e.g., promoters of cellular housekeeping genes, albumin, actin or constitutive promoters, etc. Strong constitutive promoters may be preferred for higher levels. In another embodiment of the invention an inducible promoter is been used, e.g., drug inducible promoters, such as hormone or metal promoters.

According to this invention a host cell-compatible promoter is operably linked to a structural gene or fragment thereof, encoding a polypeptide, such polypeptide can be an antigen and/or an therapeutic and/or prophylactic useful substance.

An antigen according to this invention is a molecule which modulates an immune response, when it is expressed in a desired host or cells thereof e.g., influenza antigens NP, HA, HIV gp160, human papillomavirus antigens, zona pellucida peptides, IFN-β, an autoantigen such as MBP, collagen etc. An antigen can be an entire protein comprising several epitopes, or multiply linked epitopes, from the same or different source, a single epitope, etc.

A therapeutic and/or prophylactic useful substance is any substance that treats and/or prevents diseases or conditions thereof, e.g. lymphokines, such as interleukin, tumor necrosis factor, interferon (α, β; γ, etc.) growth factors, such as nerve growth factor, and human growth hormone; tissue plasminogen activator; factor VIII:C; granulocyte-macrophage colony-stimulating factor; erythropoietin; insulin; calcitonin; thymidine kinase; and the like. Moreover selective delivery of toxic peptides (such as ricin, diphtheria toxin, or cobra venom factor) to diseased or neoplastic cells can have major therapeutic benefits. Other examples of usable therapeutic and/or prophylactic substances, are, e.g., enzymes or hormones being deficient in certain patients.

In accordance with an aspect of the present invention, there is also provided a method of treating a human disease by in vivo or ex vivo gene therapy. The types of diseases which can be treated by gene therapy include single-gene inherited disorders or multifactorial disorders or cancer and infectious diseases. A single-gene inherited disorder is a disorder resulting from mutation of a single gene (hence, single gene or monogenic disorders. A multifactorial disorder is a disorder where typically several genes are involved e.g., coronary heart disease or diabetes. The precise approach needs to be assessed in each instance by considering how specific gene products influence cellular physiology.

Cancer studies of the past two decades have established cancer as a genetic disease at the cellular level. Cancer arise through a multistage process driven by inherited and relatively frequent somatic mutation of cellular genes, followed by clonal selection of variant cells with increasingly aggressive growth properties. At least three important classes of genes—protooncogenes, tumor suppressor genes, and DNA repair genes—are targeted by mutations. The vast majority of mutations that contribute to cancer are somatic, i.e., present only in the neoplastic cells of the patient. The introduction into cancer cells of a specific gene will alter or inhibit the malignant phenotype, as shown for example in experimental data where the introduction of normal copies of tumor suppressor genes (e.g., p53 or Rb) into cancer cell lines restores normal growth properties in vitro. Thus, the present invention can be used to deliver tumor suppresor products or products absent from cancer cells to cancer cells. Another more indirect gene therapy approach is the transfer of genes encoding cytokines or other immunomodulatory products to cancer cells either outside the body (ex vivo) or directly into the patient (in vivo) to stimulate immune recognition of not only the genetically modified cancer cells, but also cancer cells that have not received the gene situated elsewhere in the body. A further approach is to transduce with bacteria according to the present invention tumor-infiltrating lymphocytes or other immune effector cells in an attempt to increase their specificity and/or reactivity against tumor cells. The introduction of suppressor genes (e.g. B or Rb) or apoptosis-inducing genes (e.g. gene for ICE) into tumor cells with the attenuated $L$ monocytogenes Δ2 mutant and the described plasma can be efficiently performed. As mentioned above, an effective gene therapy requires the transfer of DNA into recipient cells, either outside the body (ex vivo) or by direct administration to the patient (in vivo). Although in many instances, successful gene therapy will entail gene transfer to specific cells or tissues, target specificity is not always required. Suitable "generic" cells (such as fibroblasts) can serve as manufacturing plants to produce proteins that function in the circulation or are taken up by other body cells (e.g., in some enzyme storage disorders). In one embodiment of the invention, cells can be "infected" with bacteria according to the present invention outside or inside the body. *L. monocytogenes* and other bacteria according to the present invention show cell tropism with permanent cell lines in vitro which seems to depend on several internalins harbored by *L. monocytogenes* and other bacteria according to the invention, e.g., internalin A promotes invasion into epithelial cells, internalin B into hepatocytes.

*L. monocytogenes* is a Gram-positive, facultative intracellular bacterium. Preferentially as compared to Gram-negative bacteria, *L monocytogenes* lacks lipopolysaccharide (LPS) and is also able to invade a wider range of mammalian cells where it replicates in the cytosol as well (D. A. Portnoy, T. Chakraborty, W. Goebel, P. Cossart, *Infect. Immun.* 60, 1263 (1992)). Since it invades its host through the intestinal mucosal surface, *L. monocytogenes* is also a candidate for oral vaccination. Shortly after infection, bacteria are found in the spleen where professional APC are abundant. Delivery of plasmid DNA to those cells is therefore significantly enhanced by the use of suitably constructed *L. monocytogenes*. Attenuated *L. monocytogenes* cells are lysed in the cytosol of the host cell by the production of a $P_{actA}$-dependent phage lysin releasing plasmid DNA which carries different heterologous genes under the control of the human cytomegalovirus major immediate-early promoter/enhancer region ($P_{CMV}$). Beside the advantages of avoiding the use of antibiotics, lysin-mediated plasmid release is an efficient method comparable to eliminating the bacteria by antibiotic treatment.

The present invention also includes pharmaceutical products for all of the uses contemplated in the methods described herein. For example, the invention includes a pharmaceutical product comprising an attenuated invasive bacterium according to this invention. *L. monocytogenes* or other bacteria according to this invention can be administered orally (preferentially encapsulated in biodegradable polymers, e.g., PLPG), intramuscularly or intravenously, the oral administration is preferred. These bacteria can be cultured in brain heart infusion broth (BHI) or other conventional growth media, the harvested bacteria can be lyophilized, and kept at −20° C. for months. They can be also kept in a viable form at 4° C. for long periods of time (e.g., up to 3–4 months).

The dosage to be administered depends to a large extent on the condition and size of the subject being treated as well as the frequency of treatment and the route of administration. Regimens for continuing therapy, including dose and frequency may be guided by the initial response and clinical judgment.

In the foregoing and in the following examples, all temperatures are set forth uncorrected in degrees Celsius; and, unless otherwise indicated, all parts and percentages are by weight.

The entire disclosure of all applications, patents and publications, cited above and below are hereby incorporated by reference.

The present invention will be illustrated in detail in the following examples. These examples are included for illustrative purposes and should not be considered to limit the present invention.

EXAMPLES

EXAMPLE 1

Construction of the Attenuated *L monocytogenes* Mutant Strain Δ2

The attenuated *Listeria monocytogenes* mutant strain Δ2 is a derivative of the fully virulent wild-type strain EGD. The mutant lacks the entire lecithinase operon consisting of the genes mpl, actA and plcB (9) due to a site-specific chromosomal deletion. This mutant invades host cells and is released into the cytosol of the infected cells with similar efficiencies as the wild-type strain, but is impaired in intra- and intercellular movement (10). Furthermore it causes less inflammatory reaction than the wild-type strain or an actA mutant (9). Infection of BALB/c mice with the Δ2 mutant yields an i.v. $LD_{50}$ that is three logs higher than that of wild-type *L monocytogenes* EGD (i.e. $1\times10^7$ bacteria for Δ2 compared to $1\times10^4$ for EGD).

EXAMPLE 2

Introduction and Expression of Exogenous DNA

The attenuated mutant strain Δ2 of *Listeria monocytogenes* was used for the delivery of eukaryotic expression vectors which carry the cDNA for green fluorescent protein (GFP) and the genes for chloramphenicol acetyl transferase (CAT) and ovalbumin (OVA), respectively, into macrophages. The release of plasmid DNA into the host cell's cytosol was triggered by intracellular lysis of the attenuated listeriae, taking advantage of a listerial promoter that is activated in this host cell compartment. Both intracellular expression of the cloned genes and antigen presentation were achieved.

EXAMPLE 3

$P_{actA}$-driven gfp-expression is Strictly PrfA-dependent

Figure 1A:
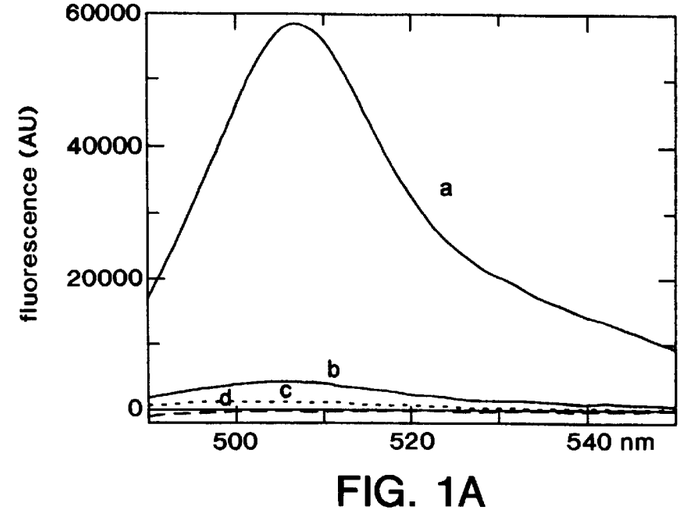
Figure 1B:
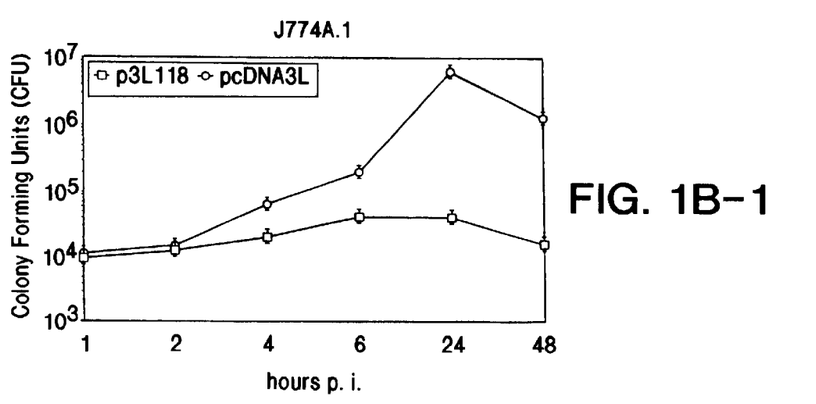
Figure 1B:
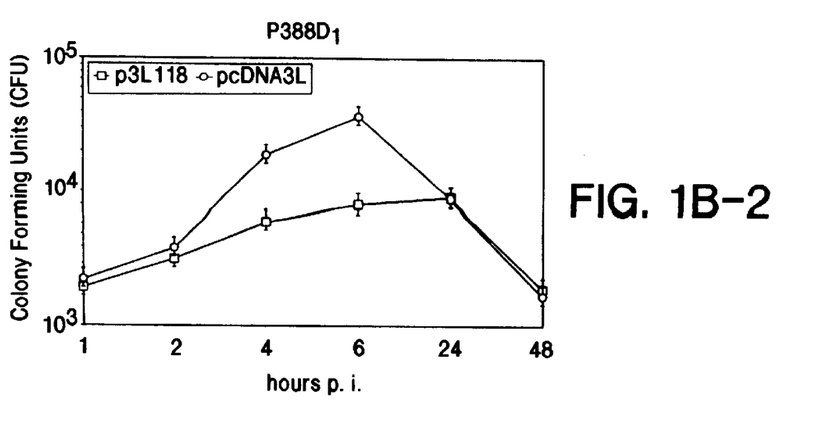

The genes actA and plcB of *L. monocytogenes* are transcribed from promoter $P_{actA}$ under the control of the transcription activator PrfA which regulates most of the known virulence genes of *L. monocytogenes* (8). The promoter $P_{actA}$ is activated preferentially in the cytosol of the infected host cells. Based on this observation, the gfp gene was inserted behind the actA promoter into the shuttle vector pLSV16 (11). Fluorescence expressed by the wild-type strain and the Δ2 mutant bacteria carrying the $P_{act}$-gfp plasmid was not significantly above the background of the EGD ΔprfA mutant carrying $P_{act}$-gfp (FIG. 1A) when the bacteria were grown in brain-heart infusion (BHI) medium. Under these growth conditions fluorescence could be detected only in an EGD strain which highly overexpresses PrfA (FIG. 1A). Fluorescent bacteria were, however, observed when the two listerial strains (EGD and the Δ2 mutant, carrying the $P_{act}$-gfp plasmid) were used to infect the macrophage-like cell line $P388D_1$ (12). Under these conditions fluorescence of the bacteria was observed approximately 2 h post infection (p.i.), i.e., at a time when most intracellular listeriae are localized in the host cell's cytosol (13). Fluorescence remained at a high level for at least 10 h. As expected, the wild-type bacteria spread into neighboring cells 6 h p.i. (13), whereas the Δ2 mutant accumulated as microcolonies within the infected cells. No fluorescence was detected in these host cells when the ΔprfA mutant strain carrying $P_{actA}$-gfp was used (data not shown), indicating that $P_{actA}$-driven gfp-expression is strictly PrfA-dependent.

EXAMPLE 4

Efficient Cytosol-Activated Production of Lysin Results in Self-Destruction of the Bacteria The lysis protein PLY118 is a late gene product of the Listeria bacteriophage A118 necessary for the release of progeny phages. PLY118 is a highly active, cell wall-hydrolyzing enzyme specific for Listeria (14). To cause self destruction of *L. monocytogenes* within host cells, the gene ply118 (encoding PLY118) was cloned downstream of the actA promoter and inserted into plasmid pcDNA3L to yield p3L118 (15). As expected, the Δ2 mutant carrying the plasmid p3L118 was not affected when the bacteria were grown in BHI. Rapid lysis of the bacteria occured, however, in the cytosol of infected J774A.1 and $P388D_1$ macrophages (FIG. 1B). The control strain carrying pcDNA3L multiplied in the cytosol of J774A.1 cells for 24 h and only for 6 h in $P388D_1$ cells. The reason for the observed decrease in the number of viable bacteria in $P388D_1$ cells between 6 h and 24 h p.i. is presently unknown (16). The difference in the intracellular growth rate between the two strains of Listeria is observed 2 h after infection, at the time when the bacteria are predominantly in the host cell's cytosol, the compartment where $P_{actA}$ is activated (see above), allowing the synthesis of the lysin. The difference in viable bacterial counts between Δ2(pcDNA3L) and Δ2(p3L118) is about one log order of magnitude in both macrophage cell lines after 6 h of intracellular growth. This difference increases to more than two orders of magnitude in J774A.1 24 h p.i., indicating an efficient cytosol-activated production of lysin resulting in self-destruction of the bacteria.

EXAMPLE 5

PLY118-Mediated Cytosolic Lysis of *L monocytogenes* leads to Efficient Release of DNA into the Cytosol of the Macrophages Plasmid-borne genes under the control of $P_{CMV}$ can be expressed in the infected host cells. Plasmids p3LGFP118, p3LCAT118 and p3LOVA118 which carry either gfp (encoding humanized green fluorescent protein, GFP), cat (encoding chloramphenicol acetyl transferase, CAT) or part of the ova gene (encoding a T cell-reactive epitope from chicken ovalbumin) under the control of $P_{CMV}$ on an otherwise identical vector plasmid were constructed. Strains containing similar plasmids without ply118 (p3LGFP, p3LCAT and p3LOVA, respectively) were used as controls (17). The functional integrity of the plasmids (i.e. expression of CAT and GFP) was tested by the transient transfection of L929 cells (with p3LGFP118, p3LGFP, p3LCAT118 and p3LCAT) (18).

EXAMPLE 6

Figure 2A:
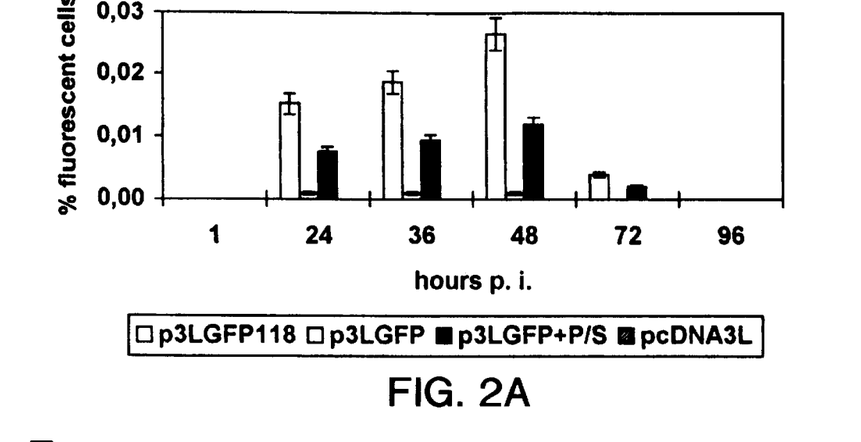

Plasmid is Transferred to the Macrophages via the Bacteria and GFP is Expressed by the Host Cells $P388D_1$ macrophages were infected with *L monocytogenes* mutant Δ2 (FIG. 2A) carrying the plasmids p3LGFP118, p3LGFP and pcDNA3L, respectively, at a dose of 50 bacteria per macrophage. We found that 1 h p.i. most of the macrophages contained one bacterium per host cell on average. The number of intracellular bacteria which carried the plasmid without ply118 increased with time, whereas that of bacteria carrying the plasmid with $P_{actA}$-ply118 remained at the initial level in the infected macrophages. The effect of the lysin on bacterial killing in the infected macrophages was significant (>90% of the bacteria were killed 6 h p.i.), but not reaching the level attained by treatment with the antibiotics penicillin and streptomycin (which killed >99% of the bacteria within 6 h p.i.). About 0.03% of the macrophages infected with the Δ2 mutant carrying p3LGFP118 showed GFP-expression between 24 and 48 h p.i. The fluorescence in the GFP-expressing macrophages was distributed over the entire cytosol and not concentrated in the bacteria as observed when GFP was expressed under the control of $P_{actA}$. This finding indicates that the plasmid is transferred to the macrophages via the bacteria and that GFP is expressed by the host cells. Infection with strain Δ2(p3LGFP) led to GFP-expression in <0.001% of the macrophages, infection with the control strain Δ2(pcDNA3L) did not show light emitting cells. Efficient delivery of plasmid DNA into the cytosol of host cells by *L. monocytogenes* is significantly stimulated by self-destruction of the bacteria by expression of PLY118 in the host's cytosol. Beside the advantages of avoiding the use of antibiotics, lysin-mediated plasmid release seems to be an efficient method comparable to eliminating the bacteria by antibiotic treatment. It was found that <0.01% of the macrophages infected with mutant Δ2(p3LGFP) expressed GFP after treatment with penicillin and streptomycin.

EXAMPLE 7

Stability of GFP in Macrophages

Macrophages expressing GFP after plasmid delivery by mutant Δ2(p3LGFP) undergo cell division and can be isolated by fluorescence-activated cell sorting (FACS) (19), followed by culturing in fresh media. A gradual loss of fluore-scence with prolonged culture time was observed. It could be shown, that the lifetime of GFP in these macrophages is long. When cycloheximide (100 μg/ml) was added to macrophages expressing GFP 48 h after infection with Δ2(p3LGFP118), fluorescence could still be observed in these cells for up to 24 h after addition of the drug. Addition of the protease inhibitors N-acetyl-L-leucinyl-L-leucinal-L-norleucinal (LLnL, 100 μg/ml, Sigma) or N-carboxybenzoxyl-L-leucinyl-L-norvalinal (MG115, 50 μg/ml, Sigma) 48 h p.i. did not increase the percentage of GFP-expressing macrophages or fluorescence in the GFP-expressing cells (data not shown). These findings shows that the relatively low percentage of GFP-expressing macrophages is not due to high instability of GFP in these cells.

EXAMPLE 8

Expression of CAT in Macrophages after Plasmid Delivery by Attenuated Suicide *Listeria monocytogenes*

Figure 2B:
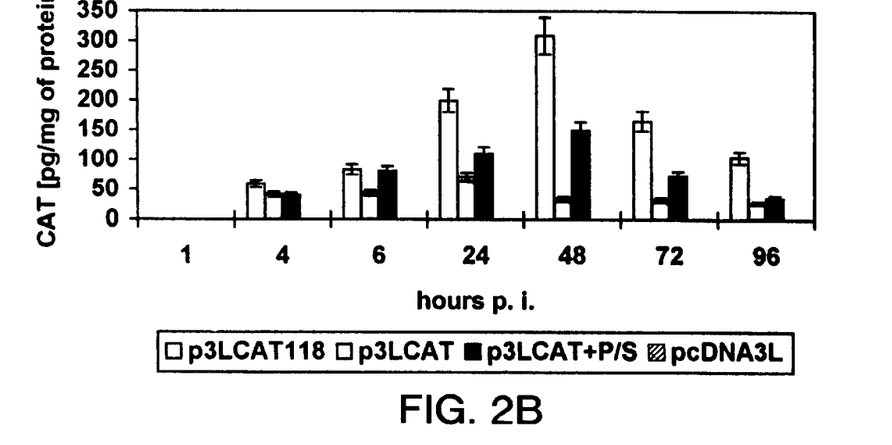

In order to determine the amount of heterologous protein expressed after plasmid delivery by the decribed procedure, P388D$_1$ macrophages were infected with mutant Δ2 carrying either p3LCAT118, p3LCAT or pcDNA3L (FIG. 2B). CAT-activity was first observed 4 h p.i. in extracts of macrophages infected with bacteria carrying p3LCAT118 and p3LCAT and reached a maximum at 48 h p.i. At this time point the CAT-activity measured in macrophages infected with Δ2(p3LCAT118) was about tenfold higher than that of cells infected with Δ2(p3LCAT). The bacteria alone did not exhibit CAT-activity when grown in BHI (data not shown), indicating that CAT was synthesized by the infected host cells after release of the plasmid DNA from the internalized listeriae. Lysis by PLY118 resulted in a more efficient plasmid release and higher CAT-activities than killing of the intracellular bacteria with antibiotics.

EXAMPLE 9

Figure 2C:
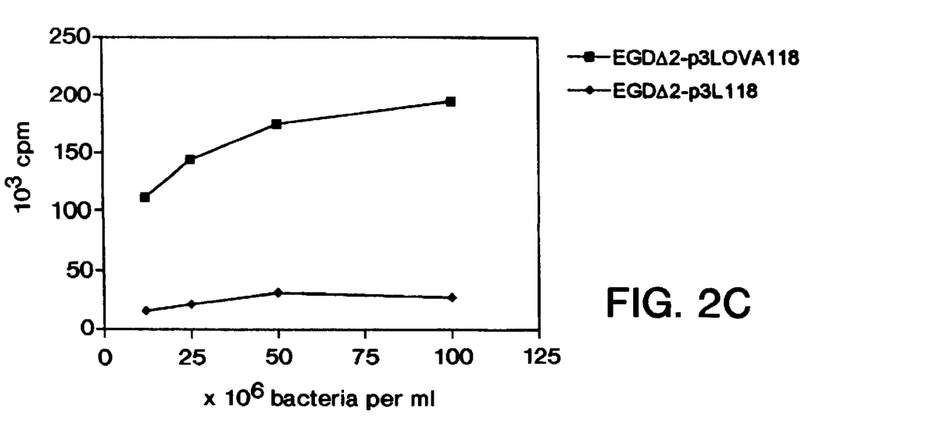

Efficiency of Antigen Presentation by Macrophages after Delivery of Antigen-Encoding Plasmid by Listeriae To test the efficiency of antigen presentation by macrophages after delivery of the antigen-encoding plasmid by listeriae, the Δ2 mutant carrying the plasmid p3LOVA118 was used. This plasmid contains part of the ova gene encoding the H-2K epitope (OVA 257–264) from chicken ovalbumine (20). Efficient presentation of this epitope in the context of MHC class I occured in bone marrow derived macrophages since the OVA-specific T-cell hybridoma RF33.70 (20) recognized macrophages infected with Δ2(p3LOVA118), but not macrophages infected with Δ2(pcDNA3L) (FIG. 2C).

EXAMPLE 10

Integration of Plasmid DNA into the Host Genome

One major problem arising from DNA-vaccination is the possible integration of plasmid DNA into the host genome. To investigate this question, advantage was taken of the neomycin phosphotransferase II gene (neo) carried on the vector pcDNA3 which was part of each vector construct. Infection of P388D$_1$ cells with Δ2(p3LCAT) at a multiplicity of infection (MOI) of 50:1 leads to the infection of most of the host cells. Selection on G418 resulted in resistant macrophage clones, which were maintained under selective conditions for over twelve weeks. In all clones, integrated plasmid p3LCAT was detected in macrophage chromosomal DNA by Southern hybridization with radioactively labelled p3LCAT, while no such sequences were present in the chromosomal DNA of uninfected P388D$_1$ cells. When the total DNAs of three different clones were cleaved with SrfI (which does not cleave vector p3LCAT) and the fragments were separated by pulse-field gel electrophoresis, a single, large-sized fragment hybridizing with the probe was detected in each case. Free purified vector DNA showed two bands (probably supercoiled and open circular form) of higher mobility under these conditions. Each of the three analyzed clones exhibited a different intensity in the "plasmid-hybridizing" large DNA-fragment, suggesting different multiple copies of the plasmid DNA incorporated into host's genome. These plasmid copies are tandemly arranged since digestion of the genomic DNA with PstI, which cleaves the plasmid into two fragments, resulted in all these cases in the same two fragments, showing the same differences in the intensity of hybridization as the uncleaved large chromosomal fragment resulting from SrfI-digestion. The calculated rate of integration in P388D$_1$ macrophages was $10^{-7}$. These data show that plasmid DNA of the type commonly used in DNA vaccination may well integrate into the genome of transfected host cells.

Safety problems which may arise as a result of DNA vaccination have already been discussed. Among those, the integration of the applied plasmid DNA into the host cell's chromosomes is of major concern (2, 21, 22). In most references, the integration of "vaccine DNA" is considered as unlikely (22), as it has not been observed when plasmid DNA was injected into mouse muscle tissue even though this DNA had persisted for more than 19 months (23). Two different studies indicate, however, a possible integration of heterologous DNA into the host cell's genome when plasmid DNA was delivered to cultured mammalian cells by *E. coli* (7) or when M13mp18 DNA was ingested orally by mice (24). The data reported here show that the plasmid p3LCAT, which is a derivative of the eukaryotic expression vector pcDNA3 commonly used for DNA vaccination, is able to integrate into the genome of the macrophage cell line P388D$_1$ at a frequency of about $10^{-7}$ as a result of the described delivery procedure. This unexpectedly high frequency of plasmid integration may be due to the high plasmid copy number delivered to most of the infected cells and may not generally hold true for all DNA vaccination strategies. It indicates, however, that integration of such plasmids may occur and thus the described system may offer a suitable and easy in vitro test system for analyzing the (possibly varying) rate of integration of plasmid DNA intended to be used as vaccines in clinical trials.

On the other hand intramuscular immunization with DNA encoding strong antigens seems to lead to destruction of most of the antigen-expressing myofibers due to a CD8+ T cell response against the antigen (25). The delivery of the plasmid DNA by the attenuated *L. monocytogenes* strain may even increase this effect since phagocytic and nonphagocytic cells of the vaccinated host which are infected by *L. monocytogenes* will evoke a strong CTL response due to the presence of listerial p60 and listeriolysin in these cells (26). Both proteins have been shown to contain very potent T cell epitopes which are presented in the context of MHC class I. Host cells infected by *L. monocytogenes*, including those with integrated plasmid sequences, should therefore finally be eradicated by the cellular immune system, thereby reducing the risk possibly associated with genomic plasmid integration.

The integration of plasmid p3LCAT in the genome of P388D$_1$ macrophages was studied as follows: Macrophage cells were infected with Δ2(p3LCAT) at a MOI of 50:1. 2 hours p.i. medium was supplemented with gentamicin (10 μg/ml), tetracycline (10 μg/ml), penicillin (100 IU/ml) and streptomycin (100 μg/ml) and, on day 5, with G418 (600 μg/ml) (Gibco). The macrophage cells were maintained with daily changes of media, until colonies resistant to G418 were detected and harvested individually. The clones were grown to confluency under selective conditions. On day 90 p.i., inserted plasmid p3LCAT was assayed by nucleic acid hybridization.

Analysis of integration of plasmid DNA was performed by pulse-field gel electrophoresis and subsequent nucleic acid hybridization: macrophage cells were embedded in agarose and treated with Proteinase K (Merck). Subsequently, DNA was digested with SrfI, separated by pulse-field gel electrophoresis, transferred to Hybond N membrane and hybridized to BamHI-linearized, $^{32}$P-labelled p3LCAT vector.

Southern Blot analysis of DNA from three independently obtained G418-resistant P388D$_1$-clones was performed. Genomic DNA was isolated, digested with PstI, separated by agarose gel electrophoresis, transferred to Hybond N membrane (Amersham) and hybridized by BamHI-linearized, $^{32}$P-labelled p3LCAT vector.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

REFERENCES AND NOTES

1. J. J. Donnelly, J. B. Ulmer, M. A. Liu, *J. Immunol. Methods* 176, 145 (1994); R. M. Conry et al., *Cancer Res.* 54, 1164 (1994); C. H. Hsu et al., *Nature Med.* 2, 540 (1996)
2. R. E. Tascon et al., *Nature Med.* 2, 888 (1996)
3. M. Corr et al., *J. Exp. Med.* 184, 1555 (1996)
4. R. R. Deck et al., *Vaccine*, 15, 71 (1997)
5. D. S. Pisetsky, *J. Immunol.* 156, 421 (1996)
6. D. R. Sizemore, A. A. Branstrom, J. C. Sadoff, *Science* 270, 299 (1995)
7. P. Couvalin, S. Goussard, C. Grillot-Courvalin, *Life Sciences* 318, 1207 (1995)
8. D. A. Portnoy, T. Chakraborty, W. Goebel, P. Cossart, *Infect, Immun.* 60, 1263 (1992)
9. N. Hauf, W. Goebel, F. Fiedler, Z. Sokolovic, M. Kuhn, *Proc. Nat. Acad. Sci. U.S.A.*, in press
10. S. Schüller, S. Kügler, W. Goebel, submitted
11. Plasmid pLSV16 [J. Bohne et al., *Mol. Microbiol,* 20, 1189 (1996)] consists of the *Escherichia coli* plasmid pUC18 and the 4,2 kb comprising, tetracycline-resistance plasmid pBCE16 which was originally isolated from *Bacillus cereus* [K. Bernhard et al., *J. Bacteriol.* 133, 897 (1978)] and replicates stably at approximately 30 copies per cell in *L. monocytogenes*. The promoterless mutant gfp gene fragment was cut out from pKEN2 as an XbaI/PstI fragment [B. P. Cormack, R. H. Valdivia, S. Falkow, *Gene* 173, 33 (1996)] and inserted in XbaI/PstI-opened pLSV16. The actA promoter region was amplified by the polymerase chain reaction (PCR) with primers PXAct5 (AGCGCTTCTAGAAGCAGCGAAAG) and PXAct3 (TCCTCTCTAGACGCTAATACAACC) carrying XbaI sites (in bold), digested with XbaI and inserted into the XbaI-site in front of the gfp gene. The correct insertion and orientation of the promoter fragment was ensured by restriction analyses with XbaI, PstI and by PCR using the PXact5 and a 3'-primer derived from the gfp gene. The resulting plasmid P$_{act}$-gfp was then electroporated into strains *L. monocytogenes* EGD, its isogenic deletion mutants ΔprfA [R. Böckmann et al., *Mol. Microbiol.* 22, 643 (1996)] and Δ2 as well as EGD(pERL3501) (J. Bohne et al., 1996)
12. The macrophage-like cell line P388D$_1$ was cultured in RPMI 1640 medium (Gibco BRL) supplemented with 10% heat-inactivated FCS (Gibco) and 2 mM L-glutamine (Gibco), referred to as complete medium, at 37° C. in a humidified 5% CO$_2$ atmosphere. $10^6$ macrophages were infected with logarithmically growing bacteria at a multiplicity of 10 per macrophage in complete medium. After incubation for 45 min, extracellular bacteria were removed by washing the cultured cells three times with PBS. For selective removal of extracellular bacteria, the infected macrophages were routinely cultured in the presence of 10 μg/ml gentamicin. At different time intervals the fluorescent bacteria were analyzed microscopically in the infected monolayer using an inverted microscope (Leica) (at 40× magnification) and data documented with a Seescan CCD camera system (INTAS).
13. E. Domann et al., *EMBO J.* 11, 1981 (1992)
14. M. J. Loessner, G. Wendlinger, S. Scherer, *Mol. Microbiol.* 16, 1231 (1995)
15. Vector pBCE16 was digested with BamHI and inserted into the single BglII-site of pCDNA3 (Invitrogen) to give plasmid pcDNA3L. The lysin ply118 from *Listeria* bacteriophage A118 was cleaved out of vector pHPL118 [M. J. Loessner et al., *Appl. Env. Microbiol.* 62, 3057 (1996)]0 with BamHI and SalI and inserted into BamHI-, SalI-precleaved pUC18 to give pUC118. The actA promoter region was PCR-amplified with primers PactA5 (5'-TCCCAGGGTACCATGCGA-3') and PactA3 (5'-TCCCACGGATCCTCCCTCC-3'), introducing sites for KpnI and BamHI, respectively (in bold). The 314bp PCR-product was digested with KpnI and BamHI and inserted into KpnI-, BamHI-precleaved pUC118. The $P_{actA}$-ply118 transcription unit of the resulting vector pActPr118 was cleaved out with PvuII and this 1470 bp fragment was inserted into the single SmaI-site of pcDNA3L. The resulting plasmid p3L118, as well as pcDNA3L, was electroporated into *L. monocytogenes* mutant Δ2.

16. A possible explanation may be a higher bactericidal activity of the $P388D_1$ macrophages compared to J774A.1 and/or an enhanced lysis of $P388D_1$ cells and the subsequent killing of the released extracellular bacteria in the gentamicin-containing medium.

17. Plasmids p3LGFP118 and p3LGFP were constructed by cleaving pCEP4-RG [Y. Wang et al., in *Bioluminescence and Chemiluminescence*, J. W. Hastings, L. J. Kricka, P. E. Stanley, Eds. (John Wiley & Sons, Chichester, 1996), pp. 419–422,] with NotI and inserting the 0.7 kb fragment containing the humanized version of the gfp-gene into NotI-precleaved vectors p3L118 and pcDNA3L, respectively. Vector p3LCAT was constructed by inserting BamHI-digested pBCE16 into the BglII-site of pcDNA/CAT (Invitrogen). Insertion of the $P_{actA}$-ply118 transcription unit of PvuII-cleaved plasmid pActPr118 into the SmaI-site of p3LCAT gave vector p3LCAT118. Plasmids p3LOVA118 and p3LOVA were constructed by inserting a linker consisting of oligonucleotides OVACODE (5'-GGCCATGAAGAGCATCATCAACTTC GAGAAGCTGAAG-3') and OVAREV (5'-GGCCCTTCA GCTTCTCGAAGTTGATGATGCTCTTCAT-3') into the NotI-sites of p3L118 and pcDNA3L. This results in expression of a peptide with the amino acid sequence MLSIINFEKLKGRSSMHLEGPIL. The insertions were verified by DNA-sequencing with the dideoxy-chain termination method. All plasmids were electroporated into *L. monocytogenes* mutant Δ2.

18. Transfections were done with the Transfection MBS Mammalian Transfection Kit (Stratagene), in accordance with the manufacturer's instructions, using the calcium phosphate precipitation method. Cells were assayed 48 h post transfection for GFP- or CAT-activity, respectively.

19. Macrophages expressing GFP were sorted with an Epics Elite ESP cell sorter (Coulter). GFP-fluorescence was analyzed using a 515 to 535 nm bandpass filter and excitation with the 488 nm line of an Argon laser. Cells sorted as positive had a more than 25-fold increase in fluorescence.

20. M. Kovacsovics-Bankowsky and K. L. Rock, *Science* 267, 243 (1995)

21. J. J. Donnelly et al., *Nature Med.* 1, 583 (1995)

22. D. E. Hassett and J. L. Whitton, *Trends Microbiol.* 4, 307 (1996); H. C. J. Ertl and Z. Xiang, *J. Immunol.* 156, 3579 (1996); F. R. Vogel and N. Sarver, *Clin. Microbiol. Rev.* 8, 406 (1995)

23. J. A. Wolff et al., *Hum. Mol. Gen.* 1, 363 (1992)

24. R. Schubbert et al., *Proc. Nat. Acad. Sci. U.S.A.* 94, 961 (1997)

25. H. L. Davis, C. L. Brazolot Millan, S. C. Watkins, *Gene Ther.* 4, 181 (1997)

26. J. T. Harty and M. J. Bevan, *J. Exp. Med.* 175, 1531–1538 (1992); E. G. Pamer, *J. Immunol.* 152, 686 (1994)

What is claimed is:

1. An attenuated invasive intracellular Listeria bacterium capable of infecting a mammalian host or host cell thereof, but having a decreased ability in intra- and intercellular movement in said host as compared to a wild type bacterium, transformed with (a) a promoter activated when said bacterium is present in the cytosol of a host cell, operably linked to a structural gene or a biologically active fragment thereof encoding a Listeria bacteriophage lysin which is lethal to the bacterium;

(b) a host cell-compatible promoter, operably linked to a structural gene or fragment thereof, encoding a polypeptide.

2. An attenuated invasive bacterium of claim 1, wherein (a) and (b) can be on the same plasmid or different plasmids.

3. An attenuated invasive bacterium of claim 1, wherein (a) can be integrated into the bacterial chromosome and (b) is on a plasmid.

4. An attenuated invasive bacterium of claim 1, wherein the bacterium is a *Listeria monocytogenes*.

5. An attenuated invasive bacterium of claim 1, wherein the bacterium lacks the lecithinase operon.

6. An attenuated invasive bacterium of claim 1, wherein the promoter in (a) is the Listeria promoter $P_{actA}$.

7. An attenuated invasive bacterium of claim 1, wherein the host cell-compatible promoter in (b) is promoter $P_{CMV}$.

8. An attenuated invasive bacterium of claim 1, wherein said lysing which is lethal to the bacterium causes autolysis of the bacterium in the cytosol of said host cell.

9. An attenuated invasive bacterium of claim 1, wherein said lysin is Lys 118.

10. A plasmid comprising (a) a promoter activated when it is present in an invasive Listeria Bacterium which is in the cytosol of a mammalian host cell, operably linked to a structural gene encoding a Listeria bacteriophage Lysin which is lethal to the bacterium.

11. A plasmid of claim 10, further comprising (b) a mammalian host cell-compatible promoter, operably linked to a structural gene encoding a protein which is an antigen.

12. A plasmid of claim 10, wherein the promoter in (a) is the Listeria promoter $P_{actA}$.

13. A plasmid of claim 11, wherein the host cell-compatible promoter in (b) is promoter $P_{CMV}$.

14. A plasmid of claim 10, wherein said lysin which is lethal to the bacterium causes autolysis of the bacterium in the cytosol of said host cell.

* * * * *

UNITED STATES PATENT AND TRADEMARK OFFICE
CERTIFICATE OF CORRECTION

PATENT NO. : 6,143,551
DATED : November 7, 2000
INVENTOR(S) : Goebel

Page 1 of 1

It is certified that error appears in the above-identified patent and that said Letters Patent is hereby corrected as shown below:

<u>Column 16, claim 8,</u>
Line 2, reads "lysing" should read -- lysin --;

<u>Column 16, claim 10,</u>
Line 2, reads "Bacterium" should read -- bacterium --;
Line 4, reads "Lysin" should read -- lysin --.

Signed and Sealed this

Ninth Day of April, 2002

Attest:

JAMES E. ROGAN
*Attesting Officer*     *Director of the United States Patent and Trademark Office*